(12) United States Patent
Rao et al.

(10) Patent No.: US 6,610,330 B2
(45) Date of Patent: Aug. 26, 2003

(54) **ANTI-DIABETIC AGENT OBTAINED FROM THE PLANT *HUMBOLDTIA DECURRENS* AND A PROCESS FOR PREPARING THE SAME**

(75) Inventors: Janaswamy Madhusudana Rao, Kerala (IN); Mangattu Achutankunju Sumathykutty, Kerala (IN); Gopalan Vijay Nair, Kerala (IN); Alathur Damodaran Damodaran, Kerala (IN); Kodandaraman Rathinam, deceased, late of Kerala (IN), by Poongothai Rathinam, legal representative; Rajagopal Sivakumar, Kerala (IN); Kottilil Mohan Das, Kerala (IN); Narayanapillai Viswanathan Nair, Kerala (IN)

(73) Assignees: Council of Scientific & Industrial Research, New Delhi (IN); Sree Chitra Tirunal Institute for Medical Sciences & Technology, Kerala (IN); Kerala Institute for Research Training and Development Studies of Scheduled Castes and Scheduled Tribes, Kerala (IN)

( * ) Notice: Subject to any disclaimer, the term of this patent is extended or adjusted under 35 U.S.C. 154(b) by 0 days.

(21) Appl. No.: 09/993,028

(22) Filed: Nov. 6, 2001

(65) Prior Publication Data

US 2002/0155176 A1 Oct. 24, 2002

Related U.S. Application Data

(63) Continuation of application No. 09/790,793, filed on Feb. 22, 2001, now abandoned.

(51) Int. Cl.$^7$ .............................................. A61K 35/78
(52) U.S. Cl. ..................................................... 424/725
(58) Field of Search ................................ 424/769, 773, 424/725, 195.1; 514/866

Primary Examiner—Christopher R. Tate
Assistant Examiner—Patricia Patten
(74) Attorney, Agent, or Firm—Jordan and Hamburg LLP

(57) ABSTRACT

The invention relates to an anti-diabetic agent obtained from the plant *Humboldtia decurrens*, an anti-diabetic formulation comprising an effect amount of the extract obtained from the plant *Humboldtia decurrens* optionally together with additives, a process for obtaining the anti-diabetic agent, and a method for treatment of diabetes.

22 Claims, No Drawings

ANTI-DIABETIC AGENT OBTAINED FROM THE PLANT *HUMBOLDTIA DECURRENS* AND A PROCESS FOR PREPARING THE SAME

This is a Continuation, of application Ser. No. 09/790, 793 filed Feb. 22, 2001, now ABN.

FIELD OF THE INVENTION

The present invention relates to a novel anti-diabetic agent, which is obtained from the plant *Humboldtia decurrens*. The invention also provides a pharmaceutical formulation comprising an effective amount of the extract obtained from the plant *Humboldtia decurrens* and useful in the treatment of diabetes. Further, a process for obtaining the extract from the said plant, and method for treatment of diabetes is also provided. The formulation acts as an inhibitory agent and helps in decreasing Blood Sugar Level.

BACKGROUND AND PRIOR ART

*Humboldtia decurrens*, (Fam: Leguminosae) is a moderate sized tree occurring in Western Ghats of Travancore. The use of this plant or any of its parts have never been disclosed to possess anti-diabetic properties as evidenced by Chemical Abstract and Patent search in literature on this genus.

OBJECTS OF THE INVENTION

The main object of the invention is to provide a novel anti-diabetic agent which is obtained from the plant *Humboldtia decurrens*.

Another object is to provide a novel anti-diabetic formulation comprising an extract obtained from the plant *Humboldtia decurrens* optionally together with pharmaceutically acceptable additives.

Yet another object of the invention is to provide a process for obtaining the extract from *Humboldtia decurrens*.

Still another object is to provide a method for treatment of diabetics.

SUMMARY OF THE INVENTION

The invention relates to an anti-diabetic agent obtained from the plant *Humboldtia decurrens*. The invention also provides a novel anti-diabetic formulation comprising an effect amount of the extract obtained from the plant *Humboldtia decurrens* optionally together with additives.

Further, the invention provides, a process for obtaining the anti-diabetic agent from the plant *Humboldtia decurrens*, and a method for treatment of diabetes.

DETAILED DESCRIPTION OF THE INVENTION

Accordingly, the invention provides a novel anti-diabetic agent obtained from the plant *Humboldtia decurrens*. Further, the invention provides a novel formulation comprising an effective amount of the extract obtained from the plant *Humboldtia decurrens*, optionally in combination with a pharmaceutically acceptable carriers, additives, diluents or excipients.

In an embodiment the active ingredient of the formulation is an extract obtained from the roots of the plant *Humboldtia decurrens*. The concentration of the extract in the formulation may be 15 to 25% by wt.

The antidiabetic formulation is devoid of toxic effects ($LD_{50}$>10 g/kg oral in rats). The unique advantage of the formulation produced by the present invention is that it provides an antidiabetic preparation from a readily available renewable source and can be used even in the crude form.

The extract which is used in the formulation of the invention is preferably obtained from the root, specifically from the root nodules of the plant *Humboldtia decurrens*.

The process for obtaining the anti-diabetic agent comprises the steps of:
(a) grinding the dried root nodules of *Humboldtia decurrens*, to fine powder,
(b) extracting the said powder with a non-polar organic solvent for a period ranging from 20–24 hrs. at a temperature in the range of 60–80° C.,
(c) optionally refluxing with an organic solvent for a period of 15 to 20 hrs., followed by evaporating the solvent to obtain a residue, and
(d) crystallising the said residue using lower aliphatic alcohol to obtain a white powder.

The extraction is effected in a Soxhlet extractor using nonpolar organic solvent such as petroleum ether or n-hexane for a period ranging from 20–24 hrs at a temperature in the range of 60–80° C. The extraction may also be effected by refluxing at a temperature of 55–65° C. for a period ranging from 15–20 hrs using organic solvents such as dichloromethane or chloroform.

As stated earlier, the extract obtained from the root of the plant *Humboldtia decurrens* is dried to obtain a find powder. Preferably this powder is used to prepare the anti-diabetic formulation. The formulation may be prepared according to any method known in the art. The formulation may be intended for oral, parenternal or other use. The formulation for oral use may be in the form of granules, particles, powders, tablets, capsules, liquid syrup, etc. In order to prepare such formulation, any pharmaceutically acceptable organic or inorganic, solid or liquid carrier, excipient, diluent may be used. The formulation may also contain sweetening agent, flavoring agent, colouring and preserving agents in order to provide pharmaceutically elegant and palatable preparations. Tablets containing the active ingredients, are prepared using the extract from roots of *Humboldtia decurrens* in combination with non-toxic pharmaceutically acceptable carriers or additives.

Suitable examples of the carriers are gelatine, vegetable oils and fats, polypropylene glycol, petroleum resin and coconut oil. Other pharmaceutically acceptable additives such as stabilizers, wetting agents, emulsifiers and the like may also be added. Liquid pharmaceutically accepted additives are selected from Tween 80, gum accacia or cottonseed oil.

The excipients used may be for example, inert diluents, such as calcium carbonate, sodium carbonate, lactose, calcium phosphate or sodium phosphate, granulating and disintegrating agents, such as corn, starch, or alginic acid; binding agents, like starch, gelatin or acacia; and lubricating agents, such as magnesium stearate, stearic acid or talc.

The tablets prepared may be uncoated or they may be coated by known techniques to delay disintegration and absorption in the gastrointestinal tract and thereby provide a sustained action over a longer period. For example, a time delay material such as glyceryl monosterate or glyceryl distearate may also be employed.

For preparation of gelatin capsules for oral use, the active ingredient (extract of the plant *Humboldtia decurrens*) is mixed with an inert solid diluent, for example, calcium carbonate, calcium phosphate or kaolin, or water or an oil medium, like peanut oil, liquid paraffin or olive oil.

Aqueous suspensions contain the active ingredient (extract of *Humboldtia decurrens*) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl, or n-propyl p-hydroxybenzoate, one or more coloring agents, one or more flavoring agents, and one or more sweetening agents, such as sucrose or saccharin. Oily suspensions may be formulated by suspending the active ingredients in a vegetable oil, for example arachbis oil, olive oil, sesame oil or coconut oil, or in a mineral oil such as liquid paraffin. The oily suspensions may contain a thickening agent, or example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of a oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gumacacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethyle sorbitan monoleate. The emulsions may also contain sweetening and flavoring agents.

Syrups and elixirs may be formulated with sweetening agents, for example, glycerol, propylene glycol, sorbitor or sucrose. Such formulations may also contain a demulcent, a preservative and flavoring and coloring agents.

The said formulation containing extract from the plant *Humboldtia decurrens* can be administered to a diabetic patient at dosage level in the range of 1 to 10 g/day. For mammals like a normal human adult, the dosage level may be in the range of 5 mg/kg wt. of the body. The specific dosage used depends upon a number of factors including requirement of the patient, severity of the condition being treated and the pharmacological activity of the formulation being used. The determination of optimum dosages for a particular patient is well-known to those skilled in the art.

The process is further illustrated by the following examples. However, these should not limit the scope of the invention.

EXAMPLE 1

The following procedure has been developed for the crude drug preparation, extraction and formulation of antidiabetic preparation from the root nodules of *Humboldtia decurrens*. Freshly collected root nodules of *Humboldtia decurrens* are dried in an airflow drier at 65° C. for 24 hours and powdered. The fine powder thus obtained is compressed to tablets of 1 g each for administration orally. The fine powder (before compressing into tablets) obtained in the above process is extracted with a solvent for a period ranging from 20–24 hours in a Soxhlet extractor. The temperature of the extraction may range from 60–80° C. The solvent may be non-polar such as non-polar hydrocarbons preferably petroleum ether, n-hexane. Alternatively, the powder is refluxed with an organic solvent, dichloromethane or chloroform for a period of 15–20 hours. The solvent is distilled off from the extract and the residue is crystallized from methanol to get a white powder.

EXAMPLE 2

The powder so obtained is then used for the formulation of required concentration using conventional pharmaceutically acceptable additives suitable for oral or parenternal administration to diabetic rats. Bioassay of the formulation/drug was performed.

EXAMPLE 3

To determine the effect of the tablets, eleven rats (Sprague-Dwaley, male) of consistent weights were selected. The fasting blood glucose concentration (mg/dl) of the rats were recorded using the Glucose Oxidase Peroxidase method. These rats were then injected with alloxan at the dose of 120 mg/kg intraperitoneal (ip) to induce experimental diabetes. After a period of 48 hours the blood glucose concentration (mg/dl) of the rats were monitored and the rats exhibiting blood glucose concentration above the normal range (>135 mg/dl) were marked diabetic and were used for further experiments. The diabetic group of rats were divided into two groups, the control group of five rats and the test group of six rats respectively. The test groups of rats were administered with the tablets at the dose of 1 g/kg orally (po), while the control groups of rats were administered with distilled water. The blood glucose concentrations of the rats of both groups were monitored at an interval of 2 hours, 4 hours and 6 hours respectively after the administration of the tablets. Results are recorded in Table 1. Results showed a fall in the blood glucose concentration at the end of 6 hours of 49% (p value<0.05), the fall being statistically significant while the control group of rats were dead at the end of 6 hours.

TABLE 1

| | Blood glucose concentration (mg/dl) | |
|---|---|---|
| Treatment | Control Vehicle *(distilled water) | Test Tablets |
| No. of Rats | 5 | 6 |
| Normal Blood Glucose concentration | **83 ± 0.8 | 75 ± 1.1 |
| Fasting Blood Glucose concentration | 81 ± 0.5 | 73.3 ± 0.8 |
| 48 hours after the administration of Alloxan | 289 ± 19 | 299 ± 22 |
| 2 hrs after the administration of Vehicle or Tablets. | 285 ± 20 | 240 ± 16 |
| 4 hrs after the administration of Vehicle or Tablets | 295 ± 21 | 214 ± 16 |

TABLE 1-continued

Blood glucose concentration (mg/dl)

| Treatment | Control Vehicle *(distilled water) | Test Tablets |
|---|---|---|
| 6 hrs after the administration of Vehicle or Tablets | 329 ± 43 | 167 ± 14 *p < 0.05 (49% inhibition) |
| 24 hrs after the administration of Vehicle or Tablets | 325 ± 43 (3 rats dead) | 244 ± 19 |
| 48 hrs after the administration of Vehicle or Tablets | 264 ± 64 (3 rats dead) | 202 + 16 |

*Statistically significant
**Values are given as Mean ± Std. Deviation

EXAMPLE 4

Glucose Tolerance Test of the Crude Drug

Ten rats of consistent weights were selected and fasted overnight. The fasting blood glucose concentration (mg/dl) of the rats were recorded. Among the 10 rats, 5 rats were marked as the test group and the rest 5 rats were marked as the control group. The test group of 5 rats were administered with the crude drug at the dose of 1 g/kg (po) with appropriate controls. Glucose at the dose of 1.5 g/kg (po) was administered to both the groups of the rats, 30 min after the administration of the drug. Blood glucose concentration: (mg/dl) of both group of rats were estimated at regular intervals of 30, 60 and 90 min respectively (Table 2). The drug showed its effect after 90 min in bringing down the blood glucose concentration in comparison to the control group of rats administered with only glucose.

TABLE 2

Blood glucose concentration (mg/dl)

| | Control (Glucose) | Test (Glucose + Drug) |
|---|---|---|
| No. of rats | 5 | 5 |
| Fasting | 65 ± 3.4 | 77 ± 9.0 |
| 30 min after the administration of Glucose/Glucose + Drug | 78 ± 5.4 | 84 ± 7.1 |
| 60 min after the administration of Glucose/Glucose + Drug | 65 ± 1.7 | 76 ± 5.4 |
| 90 min after the administration of Glucose/Glucose + Drug | 75 ± 1.5 | 56 ± 2.2* (p < 0.001) |

*Statistically significant

EXAMPLE 5

Acute Toxicity Study of the Crude Drug

Acute toxicity of the crude drug was determined by carrying out the test using 8 mice of 4 groups containing 2 mice each (one male, one female) of either sex. For the purpose of range study, a few exploratory dose at 0.6 log intervals were administered to each group of mice. On the basis of the results obtained in the preliminary assay, two additional doses spaced 0.2 of a log interal apar was selected. According to the results obtained from the experiments carried out, the $LD_{50}$ of the drug is >10 g/kg (no death). Based on the guidelines mentioned in the Principles and Methods of Toxicology by A. Wallace Hayes, the test limit for acute toxicity is generally considered to be 5 g/kg body weight. If no mortality is observed at this dose level, a higher dose level is generally not necessary as doses greater than 5 g/kg are practically non-toxic and relatively harmless (Classification of Test Materials based on Acute Toxicity-Source—"Toxicity Tests" CRC Guide Book. Toxic Substances Control Act Dominguez (ed) CRC Press Inc., Ohio 1977 pg.8.2). So no further study on the $LD_{50}$ of the drug was carried out. Results showed that the formulation with much lower concentration of the active fraction is effective in inhibiting increase in Blood Sugar Level in diabetic rats.

What is claimed is:

1. A formulation for treatment of diabetes, comprising an effective amount of an aqueous or organic solvent extract obtained from *Humboldtia decurrens* optionally in combination with at least one pharmaceutically acceptable carrier, additive, diluent, or excipient.

2. A formulation as claimed in claim 1 wherein the extract is obtained from the root nodules of *Humboldtia decurrens*.

3. A formulation as claimed in claim 1 wherein the concentration of the extract is in the range of 15 to 25 wt %.

4. A formulation as claimed in claim 1 wherein the additive is selected from Tween 80 polyoxyethylene sorbitan monooleate, gum accacia or cottonseed oil, gelatine, wetting agent, emulsifiers vegetable oils and fats, polypropylene glycol, petroleum resin and coconut oil.

5. A formulation as claimed in claim 1 made in physical forms selected from tablets, syrups, granules, capsules and elixirs.

6. A process for the preparation of an antidiabetic formulation as claimed in claim 3, said process comprising the steps of mixing the extract of *Humboldtia decurrens* with conventional pharmaceutical additives selected from solid or liquid diluents, excipients, and stabilizers.

7. A process as claimed in claim 6 wherein the extract is obtained from the root nodules of *Humboldtia decurrens*.

8. A process as claimed in claim 6 wherein the formulation contains 15 to 25 wt % of the extract.

9. A process as claimed in claim 6 wherein the excipients are selected from liquid additives such as Tween 80, gum accacia or cottonseed oil, gelatine, vegetable oils and fats, polypropylene glycol, petroleum resin and coconut oil.

10. A method for treating diabetes in a subject in need thereof comprising the step of administering an effective amount of the antidiabetic formulation of claim 1.

11. A method as claimed in claim 10 wherein the dosage of the extract is 5 gm/kg of the body weight.

12. A method as claimed in claim 10 wherein the subject is a mammal.

13. A method as claimed in claim 10 wherein the mammal is a human.

14. An anti-diabetic agent obtained from the plant *Humboldtia decurrens* wherein the agent is an aqueous or organic solvent extract obtained from the root nodules of *Humboldtia decurrens*.

15. Method of treating diabetes in mammals comprising administering to a mammal a pharmaceutically effective amount of an anti-diabetic agent obtained from the plant *Humboldtia decurrens* wherein said agent is an aqueous or organic solvent extract obtained from *Humboldtia decurrens*.

16. Method as claimed in claim 15 wherein the extract is obtained from the root nodules of *Humboldtia decurrens*.

17. Method as claimed in claim 15 wherein the extract administered is in the range of 15 to 25 wt %.

18. A process for obtaining an anti-diabetic agent from the plant *Humboldtia decurrens,* said process comprising the steps of:
(a) drying fresh root nodules of *Humboldtia decurrens* to obtain dried root nodules,
(b) grinding the dried root nodules to a fine powder,
(c) extracting the powder with a non-polar organic solvent for a period ranging from 20–24 hrs. At a temperature in a range of 60–80° C.,
(d) optionally refluxing with an organic solvent for a period of 15 to 20 hrs., followed by evaporating the solvent to obtain a residue, and
(e) crystallizing the residue using a lower aliphatic alcohol to obtain a white powder.

19. A process as claimed in claim 18 wherein the fresh root nodules of *Humboldtia decurrens* are dried at a temperature of around 65° C.

20. A process as claimed in claim 18 wherein the non-polar organic solvent used for extraction is selected from the group comprising petroleum ether and n-hexane.

21. A process as claimed in claim 18 wherein the organic solvent used for refluxing is selected from the group comprising dichloroethane and chloroform.

22. A process as claimed in claim 18 wherein the lower aliphatic alcohol is methanol.

* * * * *